(12) United States Patent
Katsnelson et al.

(10) Patent No.: US 10,556,108 B1
(45) Date of Patent: Feb. 11, 2020

(54) MULTICHANNEL APPARATUS FOR VAGUS NERVE STIMULATION

(71) Applicants: Yakov Katsnelson, Doylestown, PA (US); Hank Beckhoff, Doylestown, PA (US); Alexander Stuchenkov, Saint-Petersburg (RU); Vladimir Chuev, St. Petersburg (RU)

(72) Inventors: Yakov Katsnelson, Doylestown, PA (US); Hank Beckhoff, Doylestown, PA (US); Alexander Stuchenkov, Saint-Petersburg (RU); Vladimir Chuev, St. Petersburg (RU)

( * ) Notice: Subject to any disclaimer, the term of this patent is extended or adjusted under 35 U.S.C. 154(b) by 0 days.

(21) Appl. No.: 16/182,647

(22) Filed: Nov. 7, 2018

(51) Int. Cl.
*A61N 1/36* (2006.01)
*A61N 1/04* (2006.01)

(52) U.S. Cl.
CPC ......... *A61N 1/3603* (2017.08); *A61N 1/0456* (2013.01)

(58) Field of Classification Search
CPC ................ A61N 1/3603; A61N 1/0456; A61N 1/36038; A61N 1/0541; A61N 1/36036
USPC .......................................................... 607/74
See application file for complete search history.

(56) References Cited

U.S. PATENT DOCUMENTS

| 8,843,210 | B2 | 9/2014 | Simon et al. | |
| 8,874,205 | B2 | 10/2014 | Simon et al. | |
| 9,375,571 | B2 | 6/2016 | Errico et al. | |
| 2006/0122675 | A1 | 6/2006 | Libbus et al. | |
| 2009/0287035 | A1 | 11/2009 | Dietrich et al. | |
| 2012/0259382 | A1* | 10/2012 | Trier .................. | A61N 1/36071 607/46 |
| 2015/0005852 | A1* | 1/2015 | Hershey ............... | A61N 1/0456 607/72 |
| 2015/0360030 | A1* | 12/2015 | Cartledge .......... | A61N 1/36036 607/60 |
| 2017/0368329 | A1* | 12/2017 | Tyler .................... | A61N 1/0408 |

FOREIGN PATENT DOCUMENTS

| GB | 2526249 A | 11/2015 |
| WO | 0100273 A1 | 1/2001 |
| WO | 2016109851 A1 | 7/2016 |
| WO | 2018050773 A1 | 3/2018 |

* cited by examiner

*Primary Examiner* — Amanda K Hulbert
*Assistant Examiner* — Philip C Edwards
(74) *Attorney, Agent, or Firm* — Gearheart Law LLC

(57) ABSTRACT

A multichannel apparatus to stimulate Vagus nerves is provided. The multichannel apparatus includes a first pair of electrodes attached to an earlobe of a right external ear. A second pair of electrodes are attached to an earlobe of a left external ear. A third pair of electrodes are attached to a cymba conchae of the right external ear. A controller manages the first, second, and third pair of electrodes. The controller activates or deactivates the first, second and third electrodes; expels pulses to the right and left external ears; and provides a stimulation treatment to the Vagus nerves associated with the right and left external ears.

18 Claims, 6 Drawing Sheets

MULTICHANNEL APPARATUS FOR VAGUS NERVE STIMULATION

CLAIM OF PRIORITY

This application is a non-provisional application and claims no priority to any patent or patent application.

FIELD OF THE EMBODIMENTS

The field of the present invention and its embodiments relate to a multichannel device for noninvasive, transcutaneous auricular stimulation of Vagus nerves. The multichannel apparatus is configured to provide an electro pulse based stimulation treatment to the Vagus nerves associated with the left and right external ear structures.

BACKGROUND OF THE EMBODIMENTS

The Vagus nerve (VN) is the longest cranial nerve in the human body. It contains motor and sensory fibers and, because it passes through the neck and thorax to the abdomen, has the widest distribution in the body. Also, it contains somatic and visceral afferent fibers, as well as general and special visceral efferent fibers.

The Vagus interface the medulla oblongata with parasympathetic control of the heart, lungs, and digestive tract and is involved in the regulation of multiple systems.

Due to this wide influence on multiple systems and its important role in maintaining homeostasis, partially neuro homeostasis.

The Vagus nerve includes a sensory "auricular" branch that innervates the external ear. The upper, smaller part of the external ear lying above the crus helicis of the external ear called the cymba conchae, it is innervated exclusively by this branch; other regions of the external ear receive afferent innervation by this branch solely, or shared with other nerves, e.g., the posterior and inferior walls of the ear canal and the cavity of the concha.

The rationale of tVNS on the ear (transcutaneous auricular VNS, taVNS) is based on anatomical studies demonstrating that certain parts of the ear area (cymba conchae) have afferent VN distribution. According to the "bottom-up" mechanism of the central nervous system (CNS), electrical stimulation of these areas may produce activity changes in the VN pathway in the brain stem and central structures, producing a modulation effect similar to iVNS.

Cymba conchae stimulation produced significant activation of the "classical" central vagal projections, e.g., widespread activity in the ipsilateral nucleus of the solitary tract, bilateral spinal trigeminal nucleus, dorsal raphe, locus coeruleus, and contralateral parabrachial area, amygdala, and nucleus accumbens. Bilateral activation of the paracentral lobule was also observed.

The earlobe is innervated by the greater auricular nerve, which is a composite nerve of cervical spinal nerves 2 and 3 and projects to the nucleus cuneatus in the brainstem.

Noninvasive electrostimulation of the Vagus nerves is used to treat a number of different conditions including epilepsy, depression, anxiety, insomnia, drug and alcohol dependency, pain management, as well as to boost associative memory. Effects of known noninvasive electrostimulation techniques of the Vagus nerves are short lasting. Combination of Cymba conchae stimulation and earlobe stimulation can increase the effect and make it last longer.

Examples of the Vagus nerves stimulation mechanisms are provided below.

For instance, U.S. Pat. No. 8,843,210 pertains to treating a variety of diseases and disorders that are primarily or at least partially driven by an imbalance in neurotransmitters in the brain, such as asthma, COPD, depression, anxiety, epilepsy, fibromyalgia, and the like.

U.S. Pat. No. 8,874,205 pertains to a non-invasive electrical stimulation device shapes an elongated electric field of effect that can be oriented parallel to a long nerve, such as a Vagus nerve in a patient's neck, producing a desired physiological response in the patient.

U.S. Pat. No. 9,375,571 pertains to devices, systems and methods that allow a patient to self-treat a medical condition, such as migraine headache, by electrical noninvasive stimulation of a Vagus nerve.

US pub. 2016/109851 pertains to transdermal electrical stimulation (TES) applicators that are wearable and configured to attach to a subject's pinna (ear) and adapted to apply TES to modulate the subject's cognitive and/or physiological state.

US pub. 2018/050773 pertains to wearable device to improve exercise capacity via electrical stimulation applied to the skin of the outer ear in order to produce autonomic modulation.

Various systems and methodologies are known in the art. However, their structure and means of operation are different from the present disclosure. The other inventions fail to solve all the problems taught by the present disclosure. At least one embodiment of this invention is presented in the drawings below and will be described in more detail herein.

SUMMARY OF THE EMBODIMENTS

The present invention and its embodiments relate to a multichannel apparatus to stimulate Vagus nerves. In an example embodiment of the present invention, the multichannel apparatus may include a first pair of electrodes configured to attach to an earlobe of a right external ear. The apparatus may also include a second pair of electrodes configured to attach to an earlobe of a left external ear. Furthermore, the apparatus may include a third pair of electrodes configured to attach to a cymba conchae of the right external ear. In addition, a controller may be connected to the first, second, and third pair of electrodes. The controller may be configured to activate or deactivate the first, second and third electrodes; expel one or more pulses to the right and left external ears; and provide a stimulation treatment to the Vagus nerves associated with the right and left external ears.

In another embodiment of the present invention, a system to stimulate Vagus nerves is described. The system may include a first pair of electrodes configured to attach to an earlobe of a right external ear. The system may also include a second pair of electrodes configured to attach to an earlobe of a left external ear. Furthermore, the system may include a third pair of electrodes configured to attach to a cymba conchae of the right external ear. In addition, the system may include a controller connected to the first, second, and third pair of electrodes. The controller may be configured to activate or deactivate the first, second and third electrodes; expel one or more pulses to the right and left external ears; and provide a stimulation treatment to the Vagus nerves associated with the right and left external ears. A computing device may also be connected to the controller. The computing device may provide an interface to manage the controller.

In yet another embodiment of the present invention, a method of stimulating Vagus nerves is described. The method may include attaching a first pair of electrodes to an earlobe of a right external ear. A second pair of electrodes may be attached to an earlobe of a left external ear. A third pair of electrodes may be attached to a cymba conchae of the right external ear. A stimulation treatment of the Vagus nerves associated with the right and left external ears may be provided by activating or deactivating the first, second, and third electrodes and expelling one or more pulses to the right and left external ears.

It is an object of the present invention to provide a multichannel apparatus to stimulate the Vagus nerves associated with the right and left external ears.

It is an object of the present invention to modulate a polarity of pulses transmitted to the right and left external ears.

It is an object of the present invention to provide two channels of transmission with different modulating frequencies.

It is an object of the present invention to provide a duration of a negative polarity pulse that is three times a duration of a positive polarity pulse.

It is an object of the present invention to provide an amplitude of the positive polarity pulse that is three time an amplitude of the negative polarity pulse.

DESCRIPTION OF THE PREFERRED EMBODIMENTS

Figure 1:
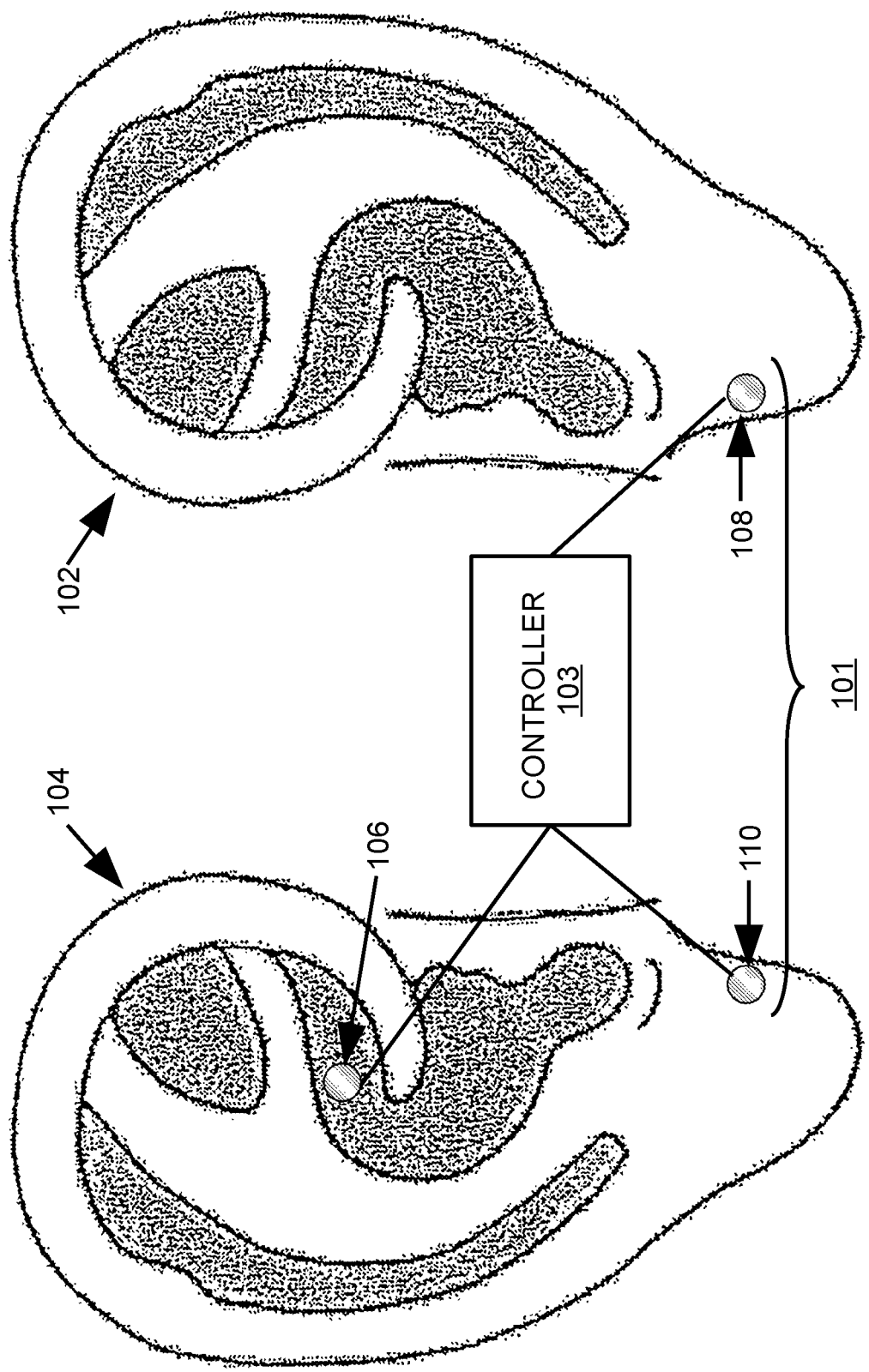
FIG. 1 shows a representation of an implementation of an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a first view of a multichannel apparatus 101 to stimulate Vagus nerves. The Vagus interface the medulla oblongata with parasympathetic control of the heart, lungs, and digestive tract and is involved in the regulation of multiple systems. Due to this wide influence on multiple systems and its important role in maintaining homeostasis, partially neuro homeostasis.

Noninvasive electrostimulation of the Vagus nerves is used to treat a number of different conditions including epilepsy, depression, anxiety, insomnia, drug and alcohol dependency, pain management, as well as to boost associative memory. However, effects of noninvasive electrostimulation of the Vagus nerves are often unstable.

The multichannel apparatus 101 may stimulate the Vagus nerves. The multichannel apparatus 101 may also improve and stabilize effects associated with the stimulation. The multichannel apparatus 101 may provide a non-invasive electrical stimulation of the Vagus nerves, earlobe stimulations of greater auricular nerve and auricular acupuncture on the external ear surface widely using for treatment of different health conditions. Resulting amelioration of illness may be provided through reticular formation and through the sympathetic and parasympathetic nervous systems.

Furthermore, electrostimulation therapies are subject to acquired tolerance from prolonged or repeated electrical stimulation. Prolonged electrostimulation is a primary cause of unstable effects associated with non-invasive electrostimulation of the Vagus nerves. The multichannel apparatus 101 may provide repeated inversions of polarity of electric pulses used to stimulate the Vagus nerves. The repeated inversions may prevent acquired tolerance associated with the electrostimulation therapy.

The multichannel apparatus 101 may include a controller 103 that manages pairs of electrodes (106, 108, and 110). The pairs of electrodes (106, 108, and 110) may allow the controller 103 to change a polarity of pulses provided to the Vagus nerves. As such, unstable effects of the electrostimulation therapy may be prevented. In an example scenario, the pair of electrodes 110 may be attached to an earlobe of a right external ear 104, the pair of electrodes 108 may be attached to an earlobe of a left external ear 102. The pair of electrodes (108 and 110) may provide a first channel of transmission for the pulses of the electrostimulation therapy The pair of electrodes 106 may be attached to a cymba conchae of the right external ear 104. The pairs of electrodes 106 and may provide a second channel of transmission for the pulses of the electrostimulation therapy.

In an example embodiment, the controller 103 may activate and/or deactivate the pairs of electrodes (106, 110, 108) to expel pulses of electrostimulation to the left and right external ears (102 and 104). The pulses may provide a stimulation treatment of the Vagus nerves associated with the left and right external ears (102 and 104). A carrier wave frequency of the pulses may be within a range of 75 to 150 kHz. An example of the carrier wave frequency may include 100 kHz. Each of the pulses emitted by the pairs of electrodes (106, 108, and 110) may include a rectangular pulse (when plotted) and a bipolar pulse.

The controller 103 may cause the pairs of electrodes (106, 108, and 110) to switch a polarity of the pulses emitted to the left and right external ears (102 and 104). A duration of a negative polarity pulse (emitted by the pairs of electrodes 106, 108, or 110) may be three times a duration of a positive polarity pulse (emitted by the pairs of electrodes 106, 108, or 110). An amplitude of a current of the positive polarity pulse may be three times an amplitude of a current of the negative polarity pulse. As such, an area underneath a chart (or a plot) of the positive polarity pulse may equal an area underneath a chart (or a plot) of the negative polarity pulse.

In an example scenario, the positive polarity pulse (provided by the pairs of electrodes 108 and 110 in channel 1) may include an amplitude of a current within a range of approximately 0.366 to 0.433 milliamps. An example of the amplitude of the current of the positive polarity pulse (provided by channel 1) may include 0.4 milliamp. The negative polarity pulse (provided by channel 1) may include an amplitude of a current within a range of approximately 0.1 to 0.166 milliamp. An example of the amplitude of the current of the negative polarity pulse (provided by channel 1) may include 0.133 milliamp.

After a change of a polarity, the previously positive polarity pulse (or currently negative polarity pulse provided by channel 1) may include an amplitude of a current within a range of approximately 0.1 to 0.166 milliamp. An example of the amplitude of the current of the previously positive polarity pulse (provided by channel 1) may include 0.133 milliamp. After the change of the polarity, the previously negative polarity pulse (or currently positive polarity pulse provided by channel 1) may include an amplitude of a current within a range of approximately 0.366 to 0.433 milliamp. An example of the amplitude of the current of the previously negative polarity pulse (provided by channel 1) may include 0.4 milliamp.

In an example scenario, the positive polarity pulse (provided by the pair of electrodes 106 in channel 2) may include an amplitude of a current within a range of approximately 1.666 to 2.3333 milliamps. An example of the amplitude of the current of the positive polarity pulse (provided by channel 2) may include 2 milliamps. The negative polarity pulse (provided by channel 2) may include an amplitude of a current within a range of approximately 0.333 to 1 milliamp. An example of the amplitude of the current of the negative polarity pulse (provided by channel 2) may include 0.666 milliamps.

After a change of a polarity, the previously positive polarity pulse (or currently negative polarity pulse provided by channel 2) may include an amplitude of a current within a range of approximately 0.333 to 1 milliamp. An example of the amplitude of the current of the previously positive polarity pulse (provided by channel 2) may include 0.666 milliamp. After the change of the polarity, the previously negative polarity pulse (or currently positive polarity pulse provided by channel 2) may include an amplitude of a current within a range of approximately 1.666 to 2.333 milliamps. An example of the amplitude of the current of the previously negative polarity pulse (provided by channel 2) may include 2 milliamps.

Furthermore, a modulation index of each of the pulses is in a range of approximately 50% to 100%. An example of the modulation index may include 75%. A duration of a modulation of the pulses may include a range of approximately 60 to 90 seconds. An example of the duration of the modulation may be 75 seconds.

The pairs of electrodes (108 and 110) attached to the earlobe of the right and left external ears (102 and 104) may provide the first channel of transmission of the electrostimulation pulses. The controller 103 may cause the pair of electrodes (108 and 110) to transmit the pulse(s) within a modulating frequency in a range of approximately 7.5 to 9.5 Hz. An example of the modulating frequency may include 8.8 Hz The pairs of electrodes 106 attached to the cymba conchae may provide the second channel of transmission of the electrostimulation pulses. The controller 103 may cause the pairs of electrodes 106 to transmit the pulse(s) within a modulating frequency in a range of approximately 5.5 to 6.5 kHz. An example of the modulating frequency may include 6 kHz.

An example of the duration of the modulation of each of the pulses may be 75 seconds. A time of treatment (or a total time of modulations of pulses) may be within a range of 22.5 minutes to 67.5 minutes. Examples of the time of treatment may include 22.5 minutes, 45 minutes, or 67.5 minutes.

Figure 2A:
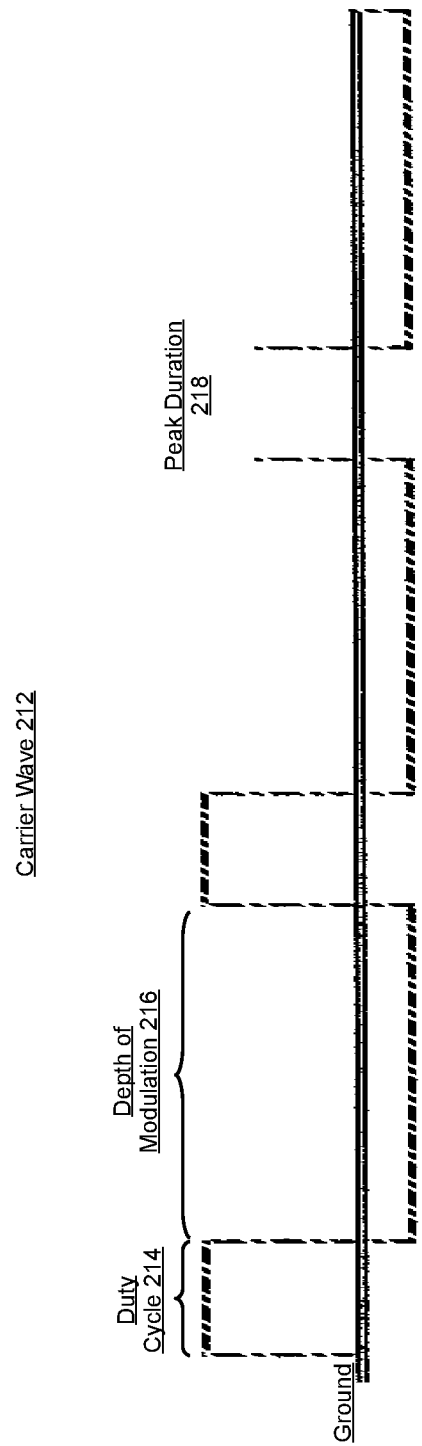
FIGS. 2A-2C show waveform charts of a carrier wave associated with embodiments of the present invention.
Figure 2B:
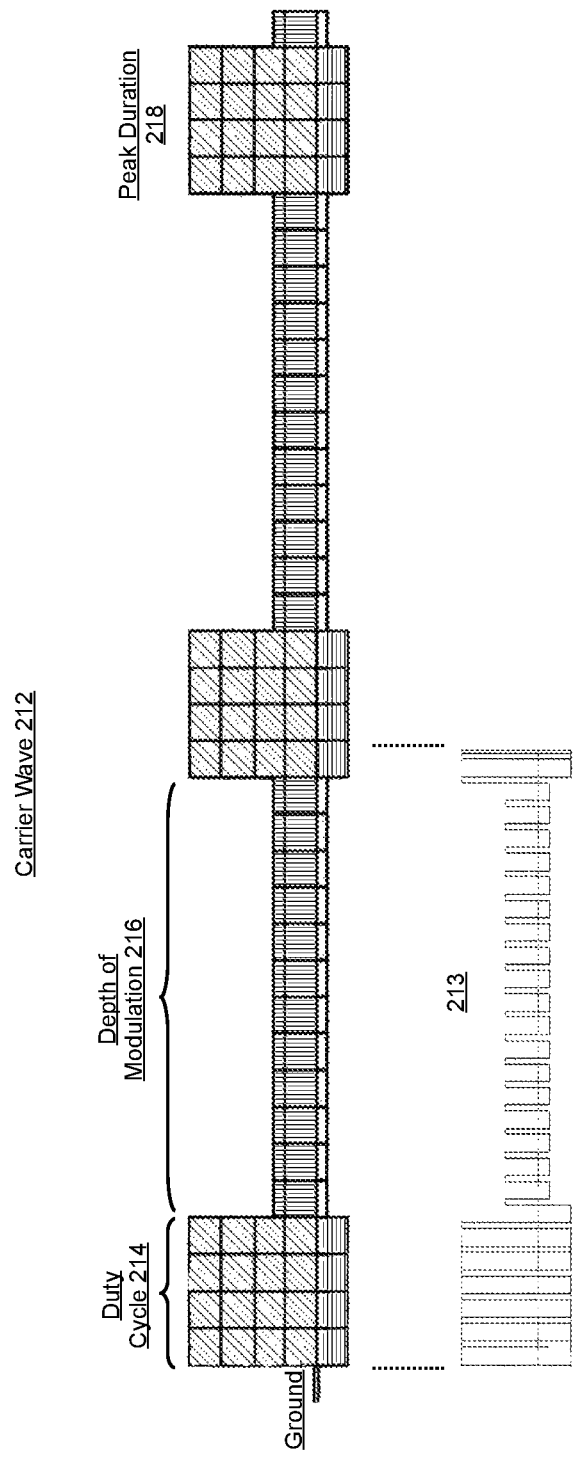
Figure 2C:
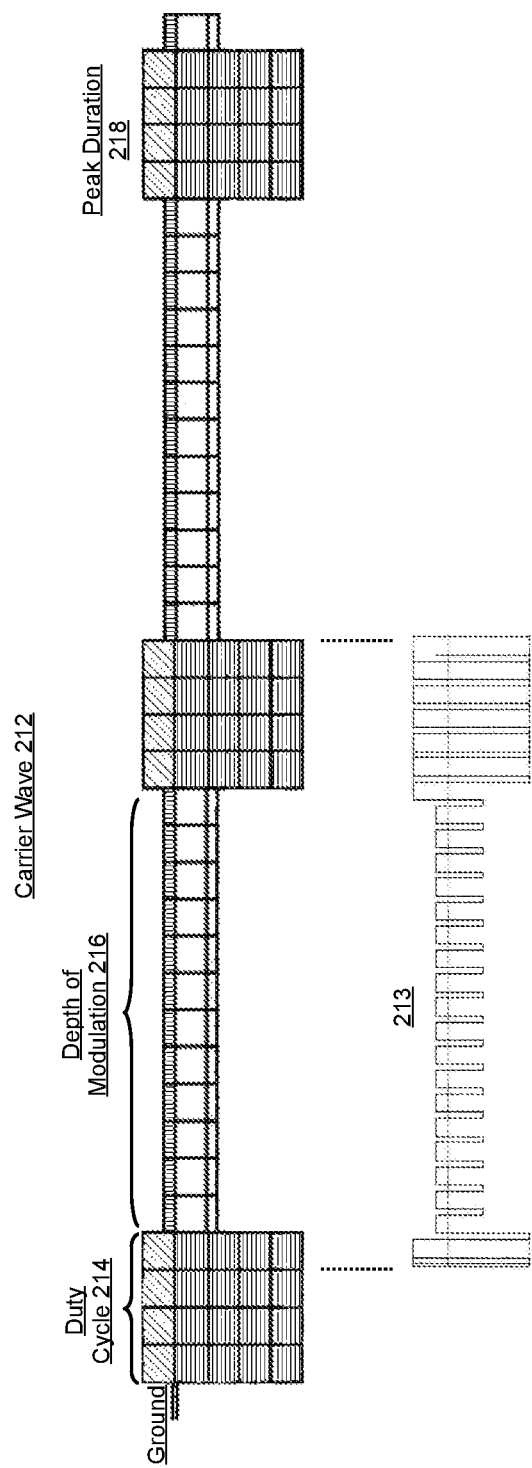

FIGS. 2A-2C show waveform charts of a carrier wave 212 associated with the multichannel apparatus 101. FIG. 2A shows the carrier wave 212 associated pulses of the electrostimulation therapy. The carrier wave 212 may include a number of parameters. For example, the carrier wave 212 may include a duty cycle 214 and a modulation index 216. An example of the duty cycle 214 may include 25%. An example of the modulation index 216 may be 75%. The carrier wave 212 may also include a peak duration 218. An example of the peak duration may include 2.5 microseconds.

FIG. 2B shows another example of the carrier wave 212. In an example scenario, the first channel of the pairs of electrodes (108, 110) may provide pulse(s) of the carrier wave 212. The carrier wave 212 may include a pulse 213. The pulse 213 may have a positive polarity with a modulating frequency of 8.8 Hz. The pulse 213 and others may be rectangular (when plotted) and bipolar. An amplitude of the positive polarity pulses may be three times an amplitude of the negative polarity pulses. As such, an area underneath a chart of the positive polarity pulse equals an area underneath a chart of the negative polarity pulse. Furthermore, the duty cycle 214 of the carrier wave may include 25%. The modulation index 216 of the carrier wave may include 75%. The peak duration 218 of the carrier wave 212 transmitted through channel 1 may equal 28.4 milliseconds.

An amplitude of a current of the positive polarity not modulated pulse may equal 0.4 milliamps. The amplitude of the current of the negative polarity not modulated pulse may equal 0.13 milliamps. The amplitude of the current of the positive polarity modulated pulse may equal 0.1 milliamps. The amplitude of the current of the negative polarity modulated pulse may equal 0.03 milliamps. A duration of the modulation may equal 75 seconds.

In another example scenario, the second channel of the pair of electrodes 106 may provide pulse(s) of the carrier wave 212. The carrier wave 212 may include a pulse 213. The pulse 213 may have a positive polarity with a modulating frequency of 6 kHz.

The pulse 213 and others may be rectangular (when plotted) and bipolar. An amplitude of the positive polarity pulses may be three times an amplitude of the negative polarity pulses. As such, an area underneath a chart of the positive polarity pulse equals an area underneath a chart of the negative polarity pulse. The duty cycle 214 of the carrier wave may include 25%. The modulation index 216 of the carrier wave may include 75%. The peak duration 218 of the carrier wave 212 transmitted through channel 2 may equal 0.04 millisecond.

An amplitude of a current of the positive polarity not modulated pulse may equal 2.0 milliamps. The amplitude of the current of the negative polarity not modulated pulse may equal 0.666 milliamps. The amplitude of the current of the positive polarity modulated pulse may equal 0.5 milliamps. The amplitude of the current of the negative polarity modulated pulse may equal 0.17 milliamps. A duration of the modulation may equal 75 seconds.

FIG. 2C shows another example of the carrier wave 212 with an inverted polarity. In an example scenario, the first channel of the pairs of electrodes 110 may provide pulse(s) of the carrier wave 212. The carrier wave 212 may include the pulse 213. The pulse 213 may have a negative polarity with a modulating frequency of 8.8 Hz. The pulse 213 and others may be rectangular (when plotted) and bipolar. An amplitude of the negative polarity pulses may be three times an amplitude of the positive polarity pulses. As such, an area underneath a chart of the negative polarity pulse equals an area underneath a chart of the positive polarity pulse. The duty cycle 214 of the carrier wave may include 25%. The modulation index 216 of the carrier wave may include 75%. The peak duration 218 of the carrier wave 212 transmitted through channel 1 may equal 28.4 milliseconds.

An amplitude of a current of the negative polarity not modulated pulse may equal 0.4 milliamps. The amplitude of the current of the positive polarity not modulated pulse may equal 0.13 milliamps. The amplitude of the current of the negative polarity modulated pulse may equal 0.1 milliamp. The amplitude of the current of the positive polarity modulated pulse may equal 0.03 milliamps. A duration of the modulation may equal 75 seconds.

In another example scenario, the second channel of the pair of electrodes (106 may provide pulse(s) of the carrier wave 212. The carrier wave 212 may include the pulse 213. The pulse 213 may have a negative polarity with a modulating frequency of 6 kHz. The pulse 213 and others may be rectangular (when plotted) and bipolar. An amplitude of the negative polarity pulses may be three times an amplitude of the positive polarity pulses. As such, an area underneath a chart of the negative polarity pulse equals an area underneath a chart of the positive polarity pulse. The duty cycle 214 of the carrier wave may include 25%. The modulation index 216 of the carrier wave may include 75%. The peak duration 218 of the carrier wave 212 transmitted through channel 2 may equal 0.04 millisecond.

An amplitude of a current of the negative polarity not modulated pulse may equal 2 milliamps. The amplitude of the current of the positive polarity not modulated pulse may equal 0.666 milliamps. The amplitude of the current of the negative polarity modulated pulse may equal 0.5 milliamps. The amplitude of the current of the positive polarity modulated pulse may equal 0.17 milliamps. A duration of the modulation may equal 75 seconds.

Figure 3:
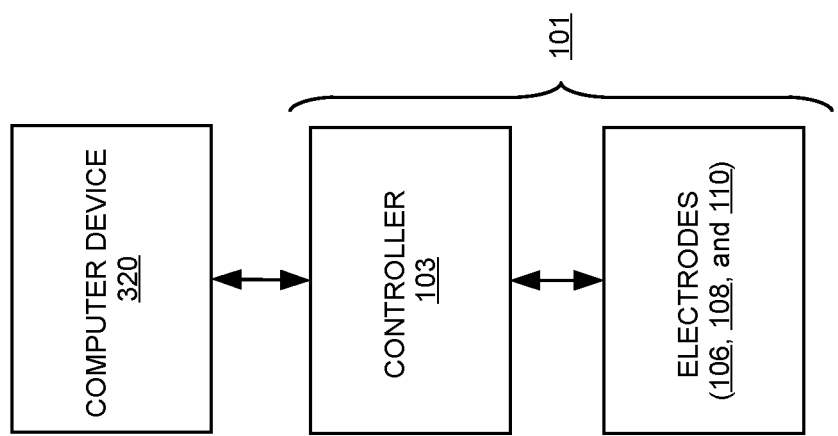
FIG. 3 shows a component view of an embodiment the present invention.

FIG. 3 shows a component view of the multichannel apparatus 101. The multichannel apparatus 101 may include a controller 103 and the pairs of electrodes (106, 108, and 110). The controller 103 may activate or deactivate the pairs of electrodes (106, 108, and 110) to provide an electrostimulation therapy of the Vagus nerves. The controller 103 may manage a number of parameters associated with the electrostimulation therapy such as a carrier wave frequency of the pulses, a modulating frequency of the pulses, a duration of a positive polarity pulse compared to a duration of a negative polarity pulse, a depth of a modulation of the pulses, an amplitude of a current of the positive polarity pulse, an amplitude of a current of the negative polarity pulse, a duration of the modulation of the pulse, and/or a time of treatment, among others.

A computing device 320 may be connected with the controller 103 and allow a user to adjust some or all of the parameters associated with the treatment. The computing device 320 may provide a user interface with which the user may interact to configure the controller 103. An example of the computing device 320 may include a mobile device such as a smart watch, a smart phone, a tablet, and/or a laptop computer, among others. The computing device 320 may also include a desktop computer, a server, and/or a distributed computing system. The server and/or distributed computing system may provide the user interface (such as a website) through which the user may interact with the controller 103.

Figure 4:
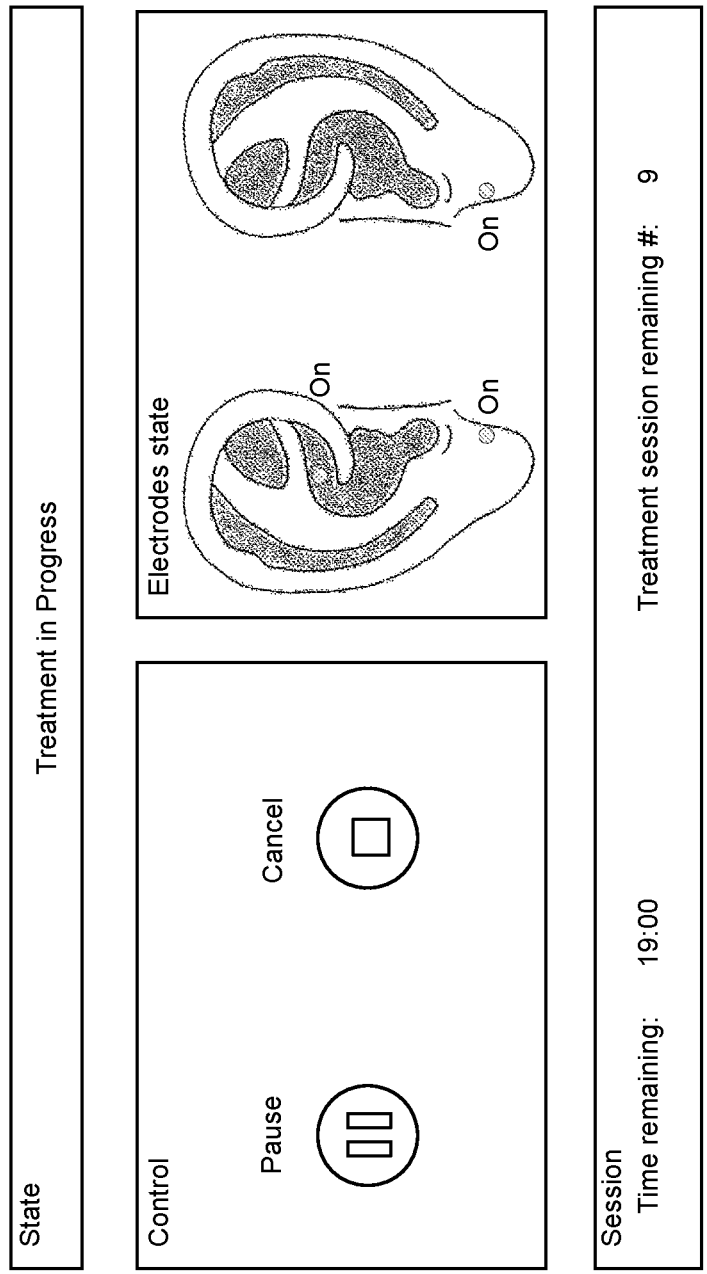
FIG. 4 shows an interface of an embodiment of the present invention.

FIG. 4 shows an interface 422 to manage the multichannel apparatus 101. The interface 422 may be provided through the computing device 320 to allow a user to interact with the controller 103. The user may be allowed to interact with the controller 103, monitor a session of an electrostimulation therapy, and adjust parameters of the session.

In an example scenario, the interface 422 may display a state associated with the electrostimulation therapy. The state may notify the user regarding a treatment in progress, a start of the treatment, and/or a stopped/ended treatment. A control box, within the interface 422, may allow the user to start, pause, continue, and/or cancel a treatment session. An electrodes state box may display the location of the pairs of the electrodes (106, 108, and 110) in relation to the structures of the right and/or left external ears. The electrodes state box may also provide active and/or de-active notification associated with each of the attached pair of electrodes. Furthermore, the interface may include a session box that display information associated with the session. For example, a remaining time associated with the session may be provided. In addition, a number of remaining sessions may also be displayed.

Previous examples of the embodiments were not provided in a limiting sense. Alternatively, the pairs of electrodes (108 and 110) may be attached to the earlobe of the left external ear 102 and earlobe of the right external ear 104 to form the first channel of transmission for the pulses of the electrostimulation therapy. The pair of electrodes 106 may be attached to the cymba conchae of the right external ear 104 to form the second channel of transmission for the pulses of the electrostimulation therapy.

A method of stimulating Vagus nerves is also described. The method may include attaching a first pair of electrodes to an earlobe of a right external ear. A second pair of electrodes may be attached to an earlobe of a left external ear. A third pair of electrodes may be attached to a cymba conchae of the right external ear. A stimulation of the Vagus nerves associated with the right and left external ears may be provided by activating or deactivating the first, second, and third electrodes and expelling one or more pulses to the right and left external ears.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A multichannel apparatus to stimulate Vagus nerves comprising:
   a first pair of electrodes configured to attach to an earlobe of a right external ear;
   a second pair of electrodes configured to attach to an earlobe of a left external ear;
   a third pair of electrodes configured to attach to a cymba conchae of the right external ear; and
   a controller coupled to the first, second, and third pair of electrodes, wherein the controller is configured to:
      activate or deactivate the first, second and third electrodes;
      expel one or more pulses to the right and left external ears, wherein the first and second pair of electrodes provide a first channel of transmission for the one or more pulses transmitted to the earlobes of the right and left external ears; and
      provide a stimulation treatment to the Vagus nerves associated with the right and left external ears,
         wherein the stimulation treatment comprises one or more pulses of electrical stimulation,
         wherein a polarity of the one or more pulses is periodically inverted,
         wherein a duration of a negative polarity pulse is about three times a duration of a positive polarity pulse,
         wherein an amplitude of the positive polarity pulse from the one or more pulses transmitted to the earlobes of the right and left external ears is within a range of approximately 0.366 to 0.433 milliamps, and wherein an amplitude of the negative polarity pulse from the one or more pulses transmitted to the earlobes of the right and left external ears is within a range of approximately 0.1 to 0.166 milliamps.

2. The apparatus of claim 1, wherein the one or more pulses include a carrier wave frequency within a range of approximately 75 to 150 kHz.

3. The apparatus of claim 1, wherein each of the one or more pulses include a rectangular pulse and a bipolar pulse.

4. The apparatus of claim 1, wherein the amplitude of the positive polarity pulse from the one or more pulses is three times the amplitude of the negative polarity pulse from the one or more pulses.

5. The apparatus of claim 1, wherein an area underneath a chart of the positive polarity pulse from the one or more pulses equals an area underneath a chart of the negative polarity pulse from the one or more pulses.

6. The apparatus of claim 1, wherein a modulation index of each of the one or more pulses is approximately 75%.

7. The apparatus of claim 1, wherein a duration of a modulation of each of the one or more pulses is approximately within a range of 60 to 90 seconds.

8. The apparatus of claim 1, wherein the one or more pulses transmitted to the earlobes of the right and left external ears include a modulating frequency within a range of approximately 7.5 to 9.5 Hz.

9. The apparatus of claim 8, wherein one or more pulses transmitted to the earlobes of the right and left external ears include a modulating frequency of 8.8 Hz.

10. The apparatus of claim 1,
wherein the amplitude of the positive polarity pulse from the one or more pulses transmitted to the earlobes of the right and left external ears approximately equals 0.4 milliamp, and
wherein the amplitude of the positive polarity pulse approximately equals 0.133 milliamp after a change of a polarity of the positive polarity pulse.

11. The apparatus of claim 1,
wherein the amplitude of the negative polarity pulse from the one or more pulses transmitted to the earlobes of the left and right external ears approximately equals 0.133 milliamps, and
wherein the amplitude of the negative polarity pulse approximately equals 0.4 milliamp after a change of a polarity of the negative polarity pulse.

12. The apparatus of claim 1, wherein the third pair of electrodes provide a second channel of transmission for the one or more pulses transmitted to the cymba conchae of the right external ear.

13. The apparatus of claim 12, wherein the one or more pulses transmitted to the cymba conchae of the right external ear includes a modulating frequency within a range of approximately 5.5 to 6.5 kHz.

14. The apparatus of claim 13, wherein the one or more pulses transmitted to the cymba conchae of the right external ear includes a modulating frequency of 6.0 kHz.

15. The apparatus of claim 12,
wherein an amplitude of a positive polarity pulse from the one or more pulses transmitted to the cymba conchae of the right external ear approximately equals 2 milliamps, and
wherein the amplitude of the positive polarity pulse approximately equals 0.666 milliamps after a change of a polarity of the positive polarity pulse.

16. The apparatus of claim 12,
wherein an amplitude of a negative polarity pulse from the one or more pulses transmitted to the cymba conchae of the right external ear approximately equals 0.666 milliamps, and
wherein the amplitude of the negative polarity pulse approximately equals 2 milliamps after a change of a polarity of the negative polarity pulse.

17. A system to stimulate Vagus nerves comprising:
a first pair of electrodes configured to attach to an earlobe of a right external ear;
a second pair of electrodes configured to attach to an earlobe of a left external ear;
a third pair of electrodes configured to attach to a cymba conchae of the right external ear;
a controller coupled to the first, second, and third pair of electrodes, wherein the controller is configured to:
activate or deactivate the first, second and third electrodes;
expel one or more pulses to the right and left external ears, wherein the first and second pair of electrodes provide a first channel of transmission for the one or more pulses transmitted to the earlobes of the right and left external ears; and
provide a stimulation treatment to the Vagus nerves associated with the right and left external ears,
wherein the stimulation treatment comprises one or more pulses of electrical stimulation,
wherein a polarity of the one or more pulses is periodically inverted,
wherein a duration of a negative polarity pulse is about three times a duration of a positive polarity pulse,
wherein an amplitude of the positive polarity pulse from the one or more pulses transmitted to the earlobes of the right and left external ears is within a range of approximately 0.366 to 0.433 milliamps, and
wherein an amplitude of the negative polarity pulse from the one or more pulses transmitted to the earlobes of the right and left external ears is within a range of approximately 0.1 to 0.166 milliamps; and
a computing device coupled to the controller, wherein the computing device provides an interface to manage the controller.

18. A method of stimulating Vagus nerves, the method comprising:
attaching a first pair of electrodes to an earlobe of a right external ear;
attaching a second pair of electrodes to an earlobe of a left external ear;
attaching a third pair of electrodes to a cymba conchae of the right external ear;
providing a stimulation treatment of the Vagus nerves associated with the right and left external ears by activating or deactivating the first, second, and third electrodes and expelling one or more pulses to the right and left external ears, wherein the first and second pair of electrodes provide a first channel of transmission for the one or more pulses transmitted to the earlobes of the right and left external ears,
wherein a polarity of the one or more pulses is periodically inverted,
wherein a duration of a negative polarity pulse is about three times a duration of a positive polarity pulse, wherein an amplitude of the positive polarity pulse from the one or more pulses transmitted to the earlobes of the right and left external ears is within a range of approximately 0.366 to 0.433 milliamps, and wherein an amplitude of the negative polarity pulse from the one or more pulses transmitted to the earlobes of the right and left external ears is within a range of approximately 0.1 to 0.166 milliamps.

* * * * *